United States Patent [19]

Buncak

[11] 4,388,193
[45] Jun. 14, 1983

[54] METHOD AND APPARATUS FOR PERFORMING THIN-LAYER CHROMATOGRAPHY

[76] Inventor: Paul Buncak, Bahnhofstrasse 31, CH-4106 Therwil, Switzerland

[21] Appl. No.: 210,437

[22] Filed: Nov. 25, 1980

[51] Int. Cl.³ ............................................. B01D 15/08
[52] U.S. Cl. ................................. 210/658; 210/198.3
[58] Field of Search ............... 210/658, 198.3; 422/70

[56] References Cited

U.S. PATENT DOCUMENTS

| | | | |
|---|---|---|---|
| 3,113,103 | 12/1963 | Lowery | 210/198.3 |
| 3,189,541 | 6/1965 | Brenner et al. | 210/198.3 |
| 3,857,784 | 12/1974 | Martinez | 210/198.3 |
| 3,915,647 | 10/1975 | Wright | 422/70 X |
| 4,161,508 | 7/1979 | Janchen | 422/70 X |
| 4,272,381 | 6/1981 | Kremer et al. | 210/198.3 |

*Primary Examiner*—John Adee
*Attorney, Agent, or Firm*—Henderson & Sturm

[57] ABSTRACT

This invention concerns chromatography in general, and more specifically to a method and apparatus for performing thin-layer chromatography without employing capillary suction, and further to a method wherein circular and anticircular chromatographic analysis can be performed simultaneously.

11 Claims, 10 Drawing Figures

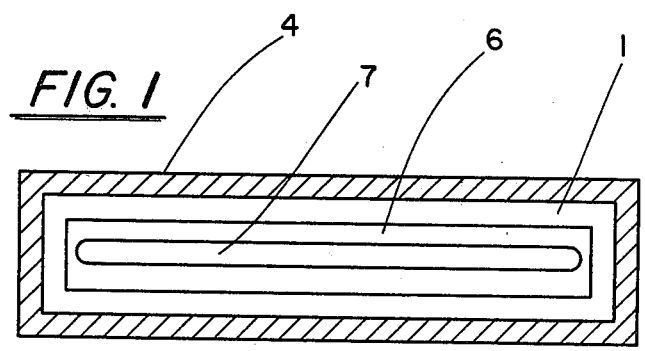
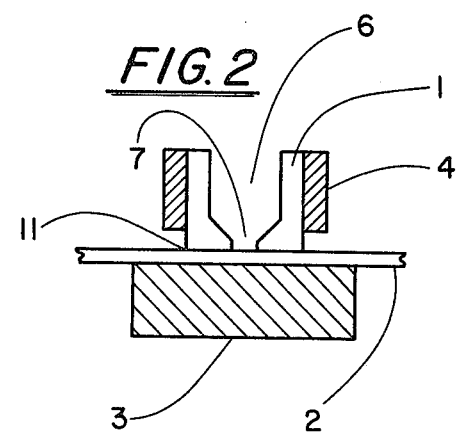
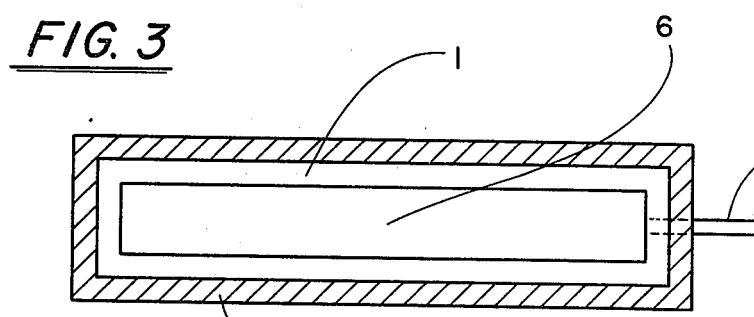
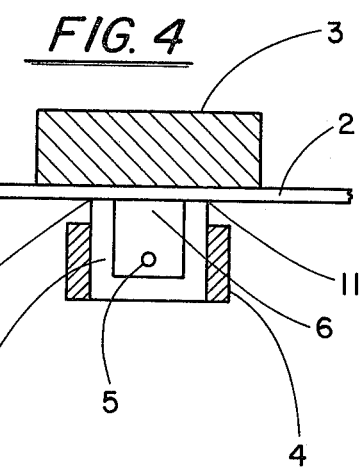
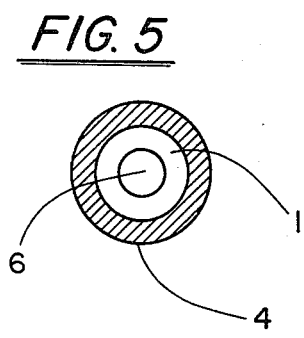
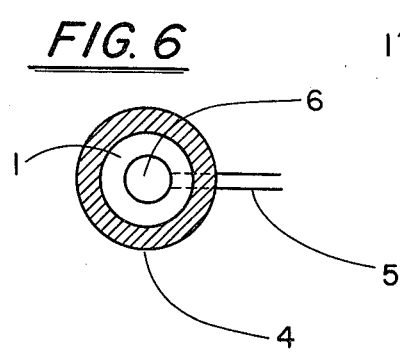

METHOD AND APPARATUS FOR PERFORMING THIN-LAYER CHROMATOGRAPHY

BACKGROUND OF THE INVENTION

Thin-layer chromatography arose from paper chromatography, which was developed in 1944 in protein research by Consden, Gordon and Martin. Both methods work with a stationary phase upon which a dissolved specimen of the material to be analyzed is placed, and with a mobile phase, a solvent in which the carrier is dipped with one end. The solvent travels by means of capillary action in the stationary phase and carries along the individual substance of the specimen at differing speeds, depending on the absorption properties. The separation of the substances is the result of the reciprocal action between the specimen of the sorption layer (stationary phase) and the developing solvent (mobile phase), as well as the gaseous phase.

In thin-layer chromatography, abbreviated as TLC, a glass plate or a sheet of plastic or aluminum is usually used as the carrier of the sorption layer.

The feed of the solvent onto the sorption layer of a carrier in a closed TLC chamber can take place in various ways. Known methods are:

(1) by dipping the edge of a TLC carrier into the flow agent;

(2) by solvent bridges made of filter paper, porous material, etc., which are in contact both with the solvent agent and also with the sorption layer of the TLC carrier;

(3) by the supplying of flow agents over a round or long capillary tube from a solvent vat directly onto the sorption layer; or (4) by a reproducible force-feed with a dosing system, e.g., pump, syringe, etc.

As is known, the travel speed of the solvent in the absorption layer decreases with the square of the distance traveled, which necessitates considerable development times in long distances to be traveled. However, the development time can be shortened by forced feeding or a reproducible overfeeding of the flow agent. This can simultaneously improve the dissolution of the separate spots and decrease the diffusion. Unfortunately, however, this method requires an expensive apparatus and was previously known and possible only for circular TLC.

Other disadvantages of previous TLC methods are the small number of ways of carrying out the method and the relatively small dosing surface. The known types of methods are:

(1) the linear TLC, i.e., the solvent travels from one side to the other side of the plate or sheet;

(2) the circular TLC, i.e., the solvent travels from the center outward in all directions; and (3) the anticircular TLC, i.e., the solvent travels from the periphery to the center of the sorption layer.

SUMMARY OF THE INVENTION

The present invention has the task of creating a method for carrying out thin-layer chromatography which makes more kinds of methods possible with a lesser consumption of solvent and a low equipment cost. In addition, a geometry gradient should be created; what this term signifies will be explained later.

This is solved by a method in accordance with the invention in which the developing solvent is conducted directly from a dosing container through an exit opening without using capillary suction action onto the sorption layer to the surface slit.

In order to accomplish the analysis rapidly, the solvent can be conducted with a certain super pressure through a feed line from a storage container into the dosing container.

An apparatus is suitable for carrying out the method of the invention which is characterized in that the dosing container has the shape of an open or closed vat with a flat support surface and at least one exit opening therein.

Other advantageous characteristics of method and apparatus are presented in the claims.

The method of the invention and embodiments of the apparatus for carrying out the method are explained in the following description with reference made to the attached drawings.

BRIEF DESCRIPTION OF THE DRAWINGS

FIG. 1 shows a top view of a dosing container for carrying out linear TLC in particular.

FIG. 2 shows a section along line 1—1.

FIGS. 3 and 4 show analogous views of a closed dosing container with forced feed, in particular for carrying out the TLC from below.

FIGS. 5 and 6 show round dosing containers for circular TLC with (FIG. 6) and without (FIG. 5) a feed for forced dosing.

DESCRIPTION OF THE PREFERRED EMBODIMENTS

Figure 7:
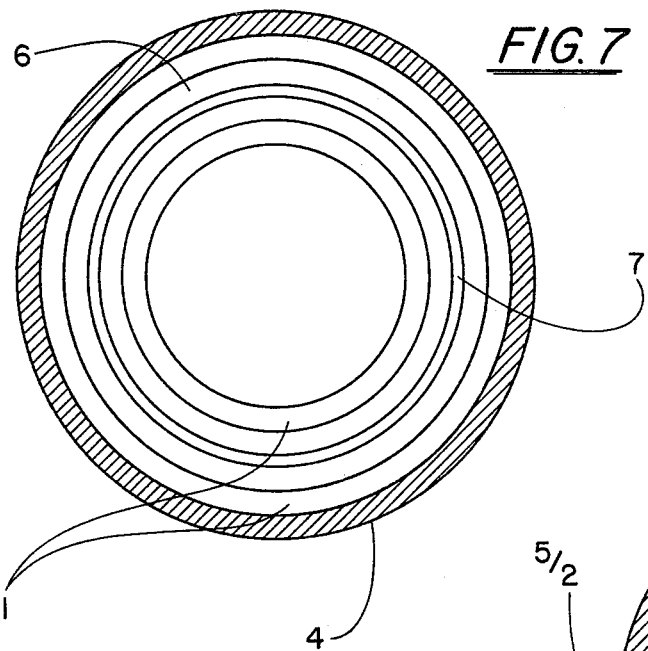
FIGS. 7 and 8 also show a top view and a section of a dosing container, this time for simultaneously carrying out circular and anticircular TLC.

Referring now to the drawings, wherein like reference numerals designate identical or corresponding parts throughout the several views, FIG. 1 shows a dosing container 1 for carrying out a linear TLC. The dosing container 1 has the form of a longitudinal vat 6 open on both sides.

Support surface 11 of vat 6 is a very precisely polished flat surface. An exit opening 7 runs parallel to the longitudinal axis of vat 6 of dosing container 1 and has the form of a slit which is approximately as long as the inner dimension of vat 6.

Vat 6 of dosing container 1 is surrounded by a metal jacket 4 made of ferromagnetic material. Dosing container 1 lies with its support surface 11 on the sorption layer of TLC plate 2, under which a magnet 3 with adjustable traction is located.

FIGS. 3 and 4 show a variation of the apparatus in which the dosing container 1 is put on TLC layer 2 from below. For this, a vat 6 is used which is open on one side and whose edges 11 function as the support surface and are accordingly ground flat. Thus, the entire width of vat 6 corresponds to the exit opening 7. As vat 6 also has a metal jacket 4, dosing container 1 can support itself with the desired support pressure on TLC plate 2 by means of a magnet 3 fixed to the upper side of plate 2. However, this embodiment necessitates a super pressure dosing, which is accomplished by supplying the solvent from a storage container (not shown) via a hose into supply line 5.

FIG. 5 shows an embodiment of a dosing container 1 from above. It is constructed analogously to the embodiment of FIGS. 1 and 2. The round form of vat 6 is required for carrying out circular TLC.

The same applies to the alternate embodiment shown in FIG. 6, which corresponds in its embodiment to FIGS. 3 and 4.

Figure 8:
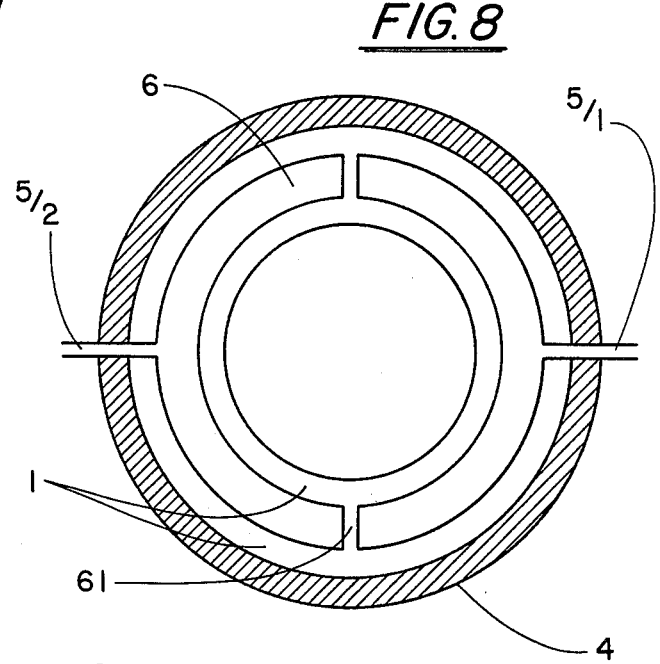
Figure 9:
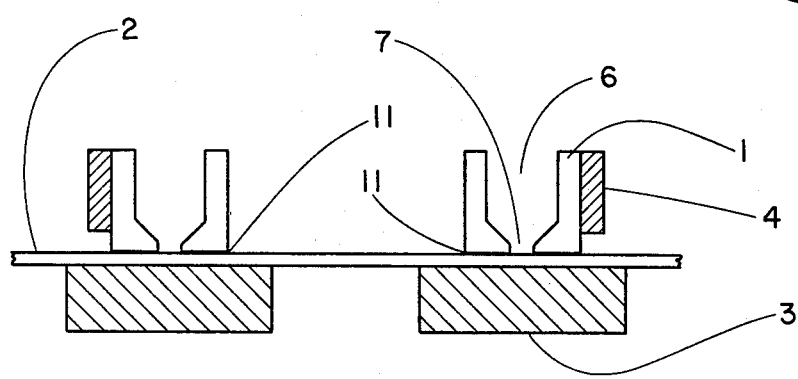
FIGS. 9 and 10 shows a closed dosing container with forced dosing for carrying circular and anticircular TLC, whereby the developing chamber is divided into two, and both partial chambers have feed lines for forced dosing.
Figure 10:
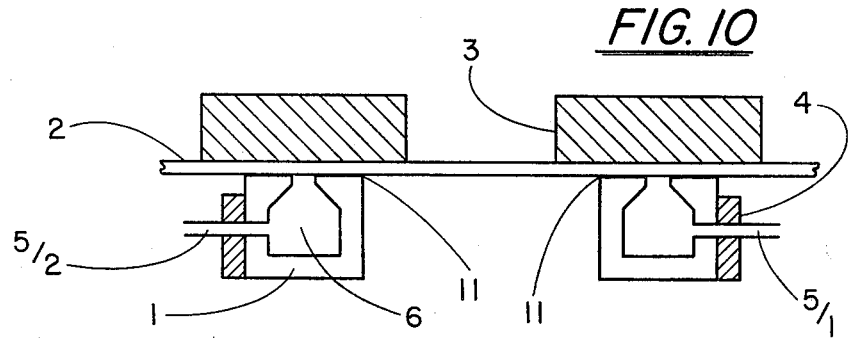

The embodiments of FIGS. 7 through 10 are suited for simultaneously executing circular and anticircular TLC. Here, too, the way of supplying the solvent in the embodiment according to FIGS. 7 and 8 corresponds to that of FIGS. 1 and 2, while the arrangement of FIGS. 9 and 10 corresponds to the way of supplying the solvent in FIGS. 3 and 4. However, the possibility is present here of subdividing vat 6 by means of dividing walls 61 into two chambers, each of which has a separate supply line 51, 52 for different solvents. Of course, the surface dosers can be held on the TLC plate or sheets not only in the way shown by means of permanent or electromagnets, but can also be fastened mechanically with adjustable support pressure. Since such a solution is purely technical and obvious to one skilled in the art, it will not be elaborated on further.

The course of the method of the invention begins, as previously described, with the application of the dissolved specimens on the sorption layer. When the specimens have been dried, the surface doser is fastened in the desired position onto the TLC plate or sheet, i.e., held by means of the attraction of a magnet located on the opposite surface of the plate or sheet. The sorption layer is now covered at an interval of 0.5–2 mm, e.g., with a glass plate. Finally, the TLC process is introduced with the supplying of the developing solvent. This occurs, depending on the embodiment utilized, by filling the solvent vat directly or via supply line 5 from the storage container.

In contrast to the known methods of chromatography, the supplying of the solvent always occurs in a kind of forced dosing, that is, the flow speed depends not only on the capillary forces of the sorption layer. This speed can be varied easily, however. The variation occurs, on the one hand, via the support pressure and the size of the support surface of the dosing container on the sorption layer; and, on the other hand, via the full amount of the solvent in the open vat of the dosing container, or via the level of the solvent in the storage container, in the case in which a dosing container with a closed vat is used.

The known and changed method steps were not cited in the description of the new method given above. To these belong, for example, the dose covering of the sorption layer, bringing the system in a chamber with reproducible saturation, time monitoring, etc.

The coating of the TLC layer with a reagent is new. This was previously done by spraying. However, it was very hard to achieve an even and reproducible amount of reagent on the entire surface of the TLC layer. The apparatus of the invention solves this methodologically by filling the reagent into the dosing container and moving the container mechanically relative to the coated surface of the TLC layer. It is advantageous to use a dosing container in accordance with FIGS. 1 through 4 for this.

It is also possible for the first time to be able to carry out simultaneously circular and anticircular development in addition to the known separate chromatographic method techniques such as linear development, circular or anticircular development. The development of a geometry gradient is also new. The inventor denotes by this term the development, i.e., the carrying out of the chromatographic method, under freely preselectable geometric conditions. Such conditions can be freely combined and comprise any desired inclination of the TLC plate between the horizontal and the vertical position, any desired shape of the exit opening of the dosing container, and any desired geometric arrangement of the dosing container on the TLC plate. The last-named condition includes, for example, the arrangement of a dosing container for linear TLC at a certain angle to the edge of the plate or sheet. During development, the initially linear flow is combined in a gradual gradient with a cross-flow of the solvent according to the angle, respectively the geometric ordering of the edges of the sorption layer to the surface doser. This geometry gradient technology makes possible for the first time a considerably improved separation of substance surfaces with very high Rf values in a shorter time and with the same solvent. Depending on the geometric shape of the surface doser and its arrangement, all transitions between linear and circular technique can be simulated (hyperbolic, parabolic functions, etc.). A surface doser subdivided into several chambers also makes it possible to perform a geometry and solvent gradient with this technique.

In dosing, the most essential advantages of the new method which can be obtained by the apparatus of the invention will now be cited once more:

greater versatility of the known method techniques;

enlargement of the dosing container surface;

performing several TLC development techiques simultaneously;

considerable reduction of the consumption of solvent and of the development time;

simplification of the excess or forced dosing;

development on any desired place of the TLC plate is possible, resulting in a better utilization of the TLC plate or sheet; and establishment of a geometry gradient.

Thus, the present invention superbly combines a simplicity of apparatus with a versatility in use.

Having thereby disclosed the subject matter of this invention, it should be obvious that many modifications, substitutions and variations of the invention are possible in light of the above teachings. It is therefore to be understood that the invention may be practiced other than as specifically described, and should be limited only to the breadth and scope of the appended claims.

I claim:

1. Method for performing a thin-layer chromatographic analysis with a plate or sheet provided with a sorption layer, whereby a dissolved specimen to be analyzed is applied at a predetermined interval from a dosing surface and is broken down into its substances while a solvent is being supplied, characterized in that the solvent is conducted directly from a dosing container through an exit opening onto the sorption layer to a surface slit without capillary suction action being used; and further characterized in that after the development is ended, the dosing container is filled with a reagent in order to make the contained materials visible, and the dosing container is moved relative to the TLC plate or sheet at a preselected pressure and speed, so that said plate or sheet is coated with the reagent.

2. Method according to claim 1, characterized in that the solvent is conducted through a supply line from a supply container into the dosing container.

3. Method according to claim 1, characterized in that the dosing container presses mechanically onto the plate or sheet, which varies the surface slit.

4. Method according to claim 1, characterized in that the dosing container is drawn onto the coated plate or sheet by a magnet.

5. Method according to claim 2, characterized in that the TLC plate is used from the lower side.

6. A device for performing a thin-layer chromatographic analysis with a plate or sheet provided with a sorption layer, whereby a dissolved specimen to be analyzed is applied at a predetermined interval from a dosing surface and is broken down into its substances while a solvent is conducted directly from a dosing container through an exit opening onto the sorption layer to a surface slit without capillary suction action being used; and further characterized in that after the development is ended, the dosing container is filled with a reagent in order to make the contained materials visible, and then the dosing container is moved relative to the TLC plate or sheet at a preselected pressure and speed, so that said plate or sheet is coated with the reagent; and still further characterized in that the dosing container has the form of a vat with a flat support surface and at least one exit opening in it.

7. Device according to claim 6, characterized in that the vat has a long, geometric shape, and the exit opening is located in the middle parallel to the longitudinal axis in the form of a slit.

8. Device according to claim 6, characterized in that the vat has an annular shape and a circular slit as exit opening in the flat support surface.

9. Device according to claim 6, characterized in that the vat is divided into a plurality of separated sovent chambers which have separate exit openings.

10. Device according to claim 6, characterized in that the device comprises a magnet which is located on the surface of the plate or sheet opposite the dosing device, and that the dosing container is jacketed at least partially with a ferromagnetic material.

11. Device according to claim 6, characterized in that the dosing container comprises a closed vat which is connected over a supply line to a storage container with solvent.

* * * * *